US006900890B1

United States Patent
Rice

(10) Patent No.: US 6,900,890 B1
(45) Date of Patent: May 31, 2005

(54) FIBER RAMAN SENSOR FOR REMOTE CHEMICAL DETECTION

(75) Inventor: Robert R. Rice, Simi Valley, CA (US)

(73) Assignee: The Boeing Company, Chicago, IL (US)

( * ) Notice: Subject to any disclaimer, the term of this patent is extended or adjusted under 35 U.S.C. 154(b) by 28 days.

(21) Appl. No.: 10/716,252

(22) Filed: Nov. 17, 2003

(51) Int. Cl.[7] ................................................. G01J 3/44
(52) U.S. Cl. ...................................... 356/301; 356/342
(58) Field of Search ................................. 356/301, 342

(56) References Cited

U.S. PATENT DOCUMENTS

| | | | | |
|---|---|---|---|---|
| 5,275,168 A | * | 1/1994 | Reintjes et al. | 356/301 |
| 5,751,415 A | * | 5/1998 | Smith et al. | 356/301 |
| 6,307,626 B1 | * | 10/2001 | Miles et al. | 356/301 |
| 6,496,634 B1 | * | 12/2002 | Levenson | 385/125 |
| 2004/0150818 A1 | * | 8/2004 | Armstrong et al. | 356/301 |

\* cited by examiner

*Primary Examiner*—F. L. Evans
*Assistant Examiner*—Kara Geisel
(74) *Attorney, Agent, or Firm*—Ingrassia Fisher & Lorenz, P.C.

(57) ABSTRACT

Methods and apparatus are provided for detecting a target substance in an atmospheric target area. The target area is illuminated with a laser beam to produce back-scatter light from substances within the target area. The back-scatter light is combined with a sample of the target substance within a hollow core fiber that has been pumped with a laser spectrum identical to the illuminating bean. If a back-scatter spectrum matches the pumped sample in the hollow core fiber, stimulated Raman scattering emissions can occur, which provide optical gain for the matching spectrum. A detector analyzes the amplified matching spectrum to identify the target substance. The disclosed apparatus may be expanded to detect multiple target substances simultaneously by using hollow core fibers containing different target samples.

16 Claims, 7 Drawing Sheets

FIBER RAMAN SENSOR FOR REMOTE CHEMICAL DETECTION

TECHNICAL FIELD

The present invention generally relates to the remote sensing of atmospheric agents, and more particularly relates to the remote sensing of particular chemical agents.

BACKGROUND

The remote detection and identification of chemical agents is an important research activity for state, local and federal governments, as well as for corporations and/or other interested individuals and groups. The threat of chemical warfare (CW) agents being used by rogue nations or terrorists, for example, is strong motivation for continuing the development of reliable early detection systems for such chemical agents. Since chemical agents are typically dispersed as aerosols or vapor to cover a wide area, an effective CW detection system should have a remote sensing capability with a high degree of sensitivity and selectivity in order to provide an early warning of the presence of a dangerous chemical agent.

Some existing chemical agent detection systems are based on laser technology, in order to identify the vibrational and rotational spectra of possible threat molecules in some way. Two detection methods in current use are known as Differential Absorption Lidar (DIAL) and Raman Back Scatter Spectroscopy. Methods such as these generally depend on the spectroscopic detection and analysis of back-scattered light signals from a distant target area, resulting from the incidence of illuminating laser beams on the potentially contaminated target area. The back-scattered signals are typically at very low power levels, however, and are generally closely spaced around the primary laser beam frequency. As such, the reliable detection of a specific gas molecule can be somewhat problematical and time-consuming with the use of conventional spectroscopic techniques.

Typically, high power lasers are used for illuminating a target area to induce a useful level of reflected back-scattered signals. Due to the low power levels and close spectral spacing of the back-scattered signals, however, the sensitivity and selectivity of the receiving apparatus of a CW detection system can be the major determining factors in the overall effectiveness and reliability of the system. That is, the detection and identification of a specific target agent, such as a nerve gas molecule for example, depends on the ability of a detection system to clearly and reliably distinguish the specific nerve gas spectrum from other reflected back-scattered signals.

Accordingly, it is desirable to provide a method and apparatus that selectively amplifies the back-scattered light signals of a specific target molecule to provide reliable detection and analysis of the target molecule. In addition, it is desirable to provide a method and apparatus with sufficient gain selectivity of back-scattered light signals to provide reliable detection and analysis of multiple target molecules simultaneously. Furthermore, other desirable features and characteristics of the present invention will become apparent from the subsequent detailed description and the appended claims, taken in conjunction with the accompanying drawings and the foregoing technical field and background.

BRIEF SUMMARY

According to various exemplary embodiments, methods and devices are provided for detecting and identifying a target substance, such as a chemical agent gas molecule, in a suspected target area. One method comprises the steps of (1) illuminating the target substance with a light, such as a laser beam, to produce reflected back-scatter signals from the target substance; (2) providing the reflected back-scatter signals to a sample of the target substance that has been pumped with a pump light essentially identical to the illuminating light; and (3) detecting stimulated Raman scattering emissions from the sample when it is a match for the characteristic spectrum of the target substance.

One exemplary embodiment of a device for detecting the presence of a target substance within a target area comprises a transmitter configured to illuminate the target area to generate reflected back-scatter light, a receiver containing a sample of the target substance and configured to selectively amplify the reflected back-scatter light from the target area, and a detector configured to verify the presence of the target substance when the amplified back-scatter light spectrum matches the spectrum of the target substance sample.

In this device embodiment, the transmitter typically includes an illuminating laser and appropriate optics for directing a laser beam to the target area. The receiver is generally in the form of a laser-pumped hollow core fiber that contains a gaseous sample of the target substance. In an exemplary embodiment, the hollow core fiber is a photonic-crystal fiber known as a holey fiber, which generally has a very low transmission loss characteristic. The exemplary device also includes optics for directing the reflected back-scatter light from the target area into the hollow core fiber. The pump laser output spectrum is essentially identical to that of the illuminating laser, so that the incidence of back-scatter light on the pumped sample of the target substance causes stimulated Raman scattering (SRS) emissions when the back-scatter light spectrum matches the characteristic spectrum of the sample. The SRS effect provides selective amplification of a matched target substance within the hollow core fiber, thereby improving the accuracy and reliability of the detection process.

In another embodiment of a target substance sensing system, the receiver can include multiple hollow core fibers, each containing a sample of a different target substance, thereby enabling the sensing system to detect multiple target substances simultaneously.

BRIEF DESCRIPTION OF THE DRAWINGS

The present invention will hereinafter be described in conjunction with the following drawing figures, wherein like numerals denote like elements.

DETAILED DESCRIPTION

Figure 1:
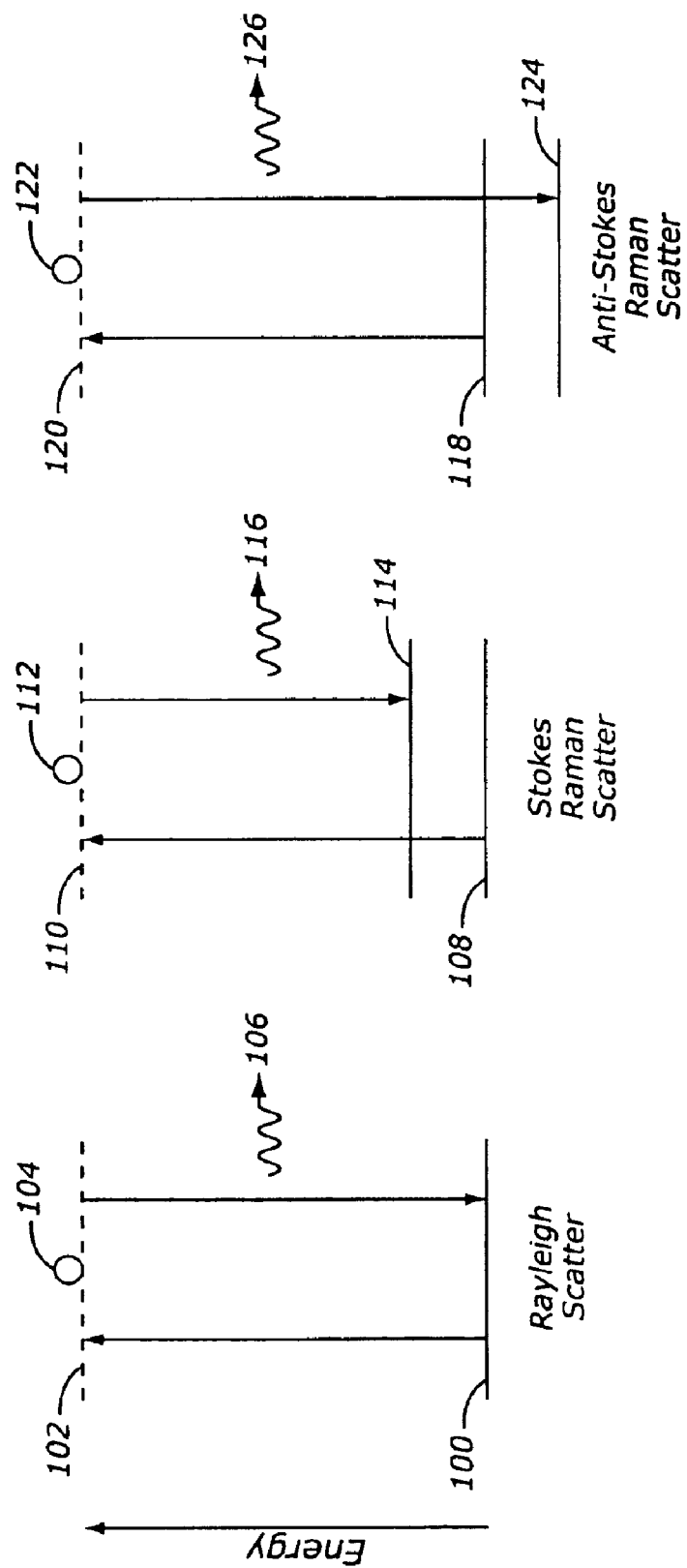
FIG. 1 is an illustration of Raman scattering.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Various embodiments of the present invention pertain to the area of remote sensing of target substances in a suspected target area Target substances of particular interest can include various classes of toxic gases, such as Soman or Tabun, which might be used in a chemical warfare attack. Remote sensing of target substances can also be useful in identifying industrial or other types of pollutants in the atmosphere. The effectiveness of a remote sensing system is dependent not only on the output power of a laser beam to illuminate a suspected target area, but also on the sensitivity and selectivity of the receiving apparatus to receive and analyze reflected back-scatter signals from the target area, so that a particular target substance can be quickly and reliably identified. The receiver apparatus disclosed herein is uniquely configured to provide a highly selective gain characteristic for the reflected back-scatter signals in order to enhance the detection and identification process of a target substance.

According to an exemplary embodiment of a remote sensing system, the phenomenon known as Raman scattering is used as a basis for generating and identifying specific spectral characteristics of a target substance, such as a specific gas molecule. The Raman effect, discovered in 1928 by C.V. Raman, can be defined as the appearance of additional lines in the spectrum of monochromatic light that has been scattered by a substance. For example, a monochromatic laser beam illuminating a target substance, such as a gas molecule, would tend to generate scattered light (photons) that would include a small percentage in the form of Raman sidebands on either side of the fundamental frequency of the illuminating laser beam. These Raman sidebands can occur when the energy of the (Raman) scattered photons is changed by the action of the illuminating laser beam, which either imparts rotational or vibrational energy, or takes energy away. These energy changes can change the frequency of the Raman scattered photons, resulting in additional corresponding spectral lines having longer and shorter wavelengths than that of the incident radiation.

When a light beam is impinged upon a substance, photons are typically absorbed by the substance and are scattered. The vast majority of these scattered photons retain the same wavelength as the incident photons, and are known as "Rayleigh scatter". At the same time, a small portion of the scattered photons are shifted to different wavelengths, as described above, and are known as "Raman scatter". Most of the Raman scattered photons are shifted to longer wavelengths, called "Stokes shift", and a smaller portion of the scattered photons are shifted to shorter wavelengths, called "anti-Stokes shift".

For illustrative purposes, a simplified energy-level diagram of Rayleigh and Raman scatter is shown in FIG. 1. In each type of scatter, it is assumed that an incident photon (not shown) has excited an electron (104, 112, 122) from a ground state (100, 108, 118) into a higher "virtual" energy level (102, 110, 120). According to light theory, the excited electron (104, 112, 122) will decay to a lower level (100, 114, 124). The energy released by this decaying action is typically in the form of a scattered photon (106, 116, 126). In Rayleigh scattering, the electron 104 decays back to the same level 100 from which it started. In both types of Raman scattering, however, the electron (112, 122) decays to a different level from where it started. Stokes Raman scattering occurs when the final energy level 114 is higher than the initial level 108, and anti-Stokes Raman scattering occurs when the final energy level 124 is lower than the starting level 118. As a result of a Stokes scattering event, the scattering molecule has gained energy in a vibrational or rotational excited state, whereas it has lost such energy as a result of an anti-Stokes scattering event. Since Stokes Raman scattering is generally much more prevalent than anti-Stokes Raman scattering, the Stokes type of scattering is generally used in Raman spectroscopy.

A Raman spectrum is a plot of the intensity of Raman scattered radiation as a function of its frequency/wavelength difference from the incident radiation (usually in units of wave numbers, $cm^{-1}$). For example, a commonly used laser material, Neodymium doped Yttrium Aluminum Garnet (Nd:YAG) typically lases at a wavelength of 1,064 nanometers. As such, its photon energy would be concentrated at a wave number of 9,398.5 $cm^{-1}$, whereas for complex target molecules, typical Raman shift values would be in the range of 100 to 2,000 $cm^{-1}$ wave numbers. Therefore, the Raman sidebands for back-scatter from target gas molecules are generally closely spaced around the incident frequency, and are typically plotted as a difference value from the incident frequency/wavelength. Moreover, the Raman shift is generally independent of the frequency of the incident radiation, which makes it very useful for identifying a target substance by spectroscopic techniques, as will be described in a later section.

Figure 2:
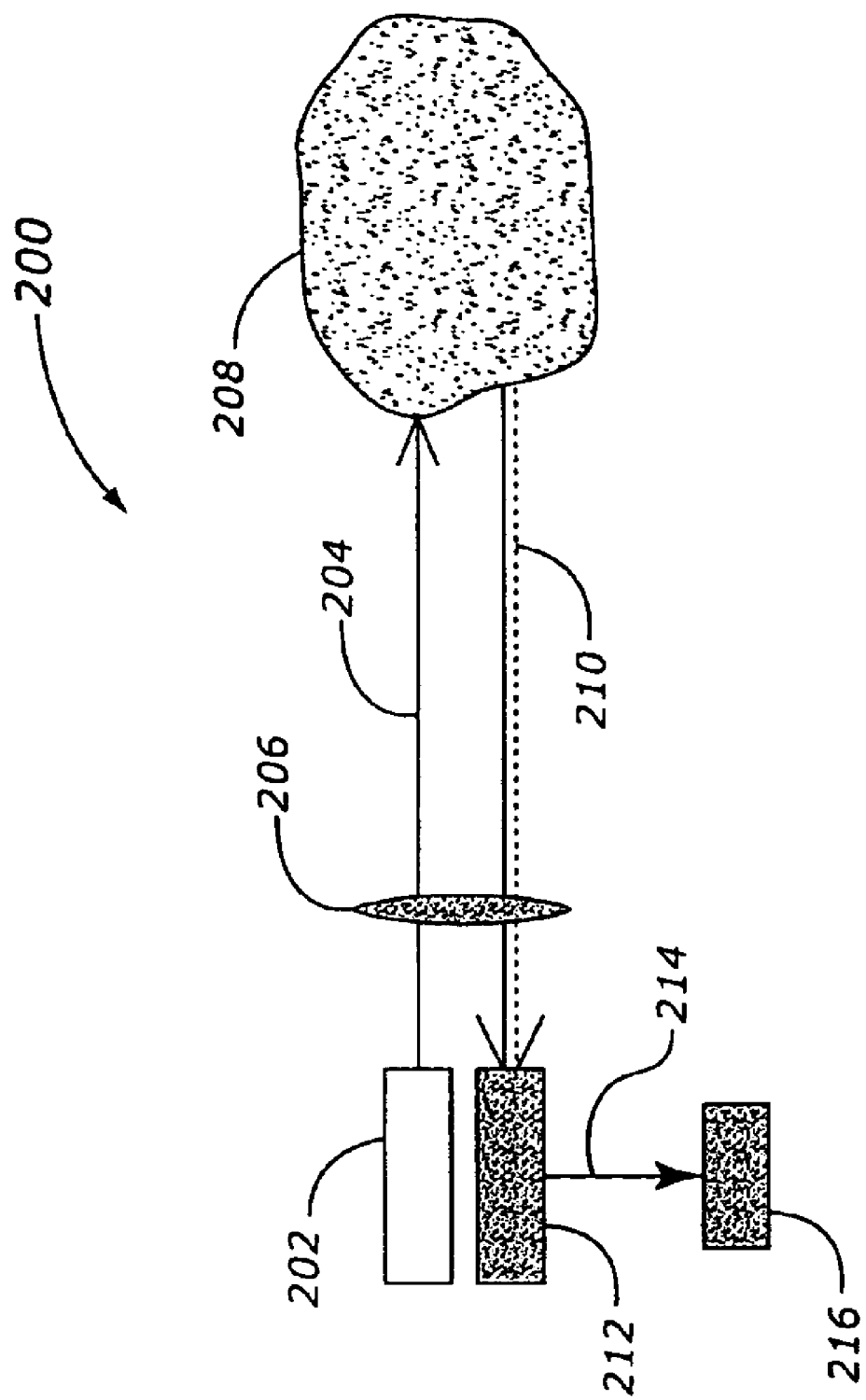
FIG. 2 is a block diagram of an exemplary embodiment of a chemical agent detection system.

In accordance with an exemplary embodiment of a remote sensing system 200, as shown in simplified block diagram form in FIG. 2, an illuminator 202 outputs a light beam 204 through an optical arrangement 206, in order to impinge light beam 204 on a suspected target area 208. Reflected scatter light 210 is collected by optical arrangement 206, and is directed into a receiver apparatus 212, which contains a sample of a known substance of interest. If reflected scatter light 210 contains a molecular match to the known substance sample, a phenomenon known as stimulated Raman scattering (SRS) can occur in receiver apparatus 212, resulting in a selective amplification of the matching molecular scatter. This process will be described in further detail below. As a result of the SRS process, receiver 212 can output an amplified scatter signal 214 with a spectrum matching that of the target substance sample. Signal 214 is then routed to a signal processor/detector 216 for spectroscopic analysis and identification.

Figure 3:
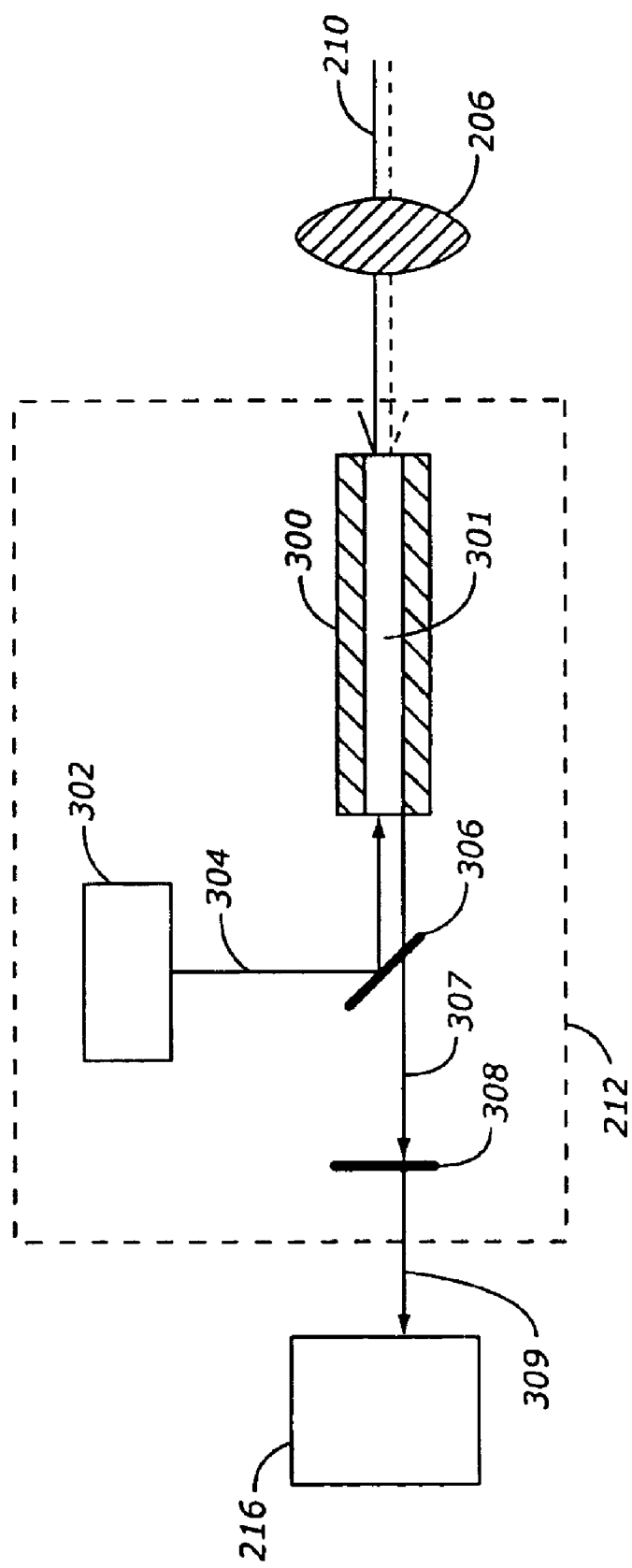
FIG. 3 is a block diagram of an exemplary embodiment of the receiver/detector portion of the chemical agent detection system in FIG. 2.

A more detailed diagram of receiver 212 and associated elements is shown in FIG. 3, with like numerals from FIG. 2 denoting like elements in FIG. 3. Reflected scatter light 210 from target area 208 (FIG. 2) is collected by optical arrangement 206, and directed into a hollow core fiber 300. While optical arrangement 206 is depicted as a single lens in the embodiments shown in FIGS. 2 and 3, an equivalent optical arrangement could include two or more lenses, in accordance with different design embodiments.

A sample of a known substance 301 for comparison with the target substance is contained within the hollow core of fiber 300, typically in gaseous form. The sample target substance may be obtained by any appropriate method, such as being supplied from a vapor reservoir (not shown). The target substance sample 301 is typically pumped within hollow core fiber 300 by a beam 304 from a pump laser 302. Pump laser 302 is typically configured to output a beam spectrum that is essentially identical to the output spectrum of illuminating laser 202. In an alternate embodiment, a single laser could be used for both illumination and pumping.

In the exemplary embodiment shown in FIG. 3, a dichroic mirror 306 is used to reflect pump beam 304 into the known substance sample 301 within the hollow core of fiber 300. However, any suitable method of pumping sample 301 can be used, as long as the pumping beam 304 spectrum matches that of the illuminating beam 204. The pumped (energized) sample 301 interacts with the reflected scatter light 210 in hollow core fiber 300. If there is a gas molecule component of scatter light 210 that spectrally matches the energized sample 301, the spectrally matched gas molecules are selectively amplified by a stimulated emissions process (SRS). As a result, an amplified emission beam 307 passes through dichroic mirror 306 to a pump filter 308, which is configured to block any residual signals at the pump laser wavelength. The filtered beam 309 is then routed to signal processor/detector 216, where filtered beam 309 can be spectroscopically analyzed to positively identify the target substance.

The operation of dichroic mirror 306 is based on a configuration having a transition wavelength value that allows dichroic mirror 306 to separate two light paths of different wavelengths. In this embodiment, pump beam 304 is reflected by dichroic mirror 306 because the wavelength of beam 304 is below the transition wavelength value, while emission beam 307 is transmitted by dichroic mirror 306 because the wavelength of emission beam 307 is above the transition wavelength value.

In an exemplary embodiment of the present invention, the illuminating laser beam 204 is generally in the form of very short pulses, in order to utilize high levels of peak power. Typically, a laser pulse incident on a potentially contaminated target area will produce a back-scatter signal that includes both the incident pulse laser wavelength and any induced Raman sidebands, with a specific set of Raman sideband wavelengths for each molecular species present. If the Raman sideband wavelengths of a back-scatter molecule are introduced into the hollow core of a fiber containing a sample of the same substance as the back-scatter molecule, and if the hollow core fiber is pumped by a laser source spectrally identical to the illuminating laser beam, the conditions for SRS are present. That is, the interaction between the vibrational and rotational energy levels of the molecules in the pumped sample and the molecules in the matching back-scatter Raman sidebands can create a regenerative feedback loop, enabling the resultant stimulated emissions to increase significantly within the hollow core fiber. As such, optical gain can occur at these specific wavelengths (Raman shifts) around the pump laser wavelength when the back-scatter molecules match the molecular structure of the target sample in the hollow core fiber. Therefore, the hollow core fiber in this exemplary embodiment can become a highly selective amplifier for light with exactly the Raman scatter spectrum as that of the known sample. Conversely, light scattered back from a different remote substance would generally experience no optical gain because its spectrum would not match the spectrum of the hollow core Raman fiber amplifier.

To further enhance the optical gain characteristics of the hollow core fiber embodiment described above, a type of photonic-crystal fiber, known as holey fiber, can be used as the hollow core medium. This recently developed holey fiber is typically configured with a pattern of tiny air holes running along its length. The purpose of the air holes is to guide light through the holey fiber in a manner that significantly reduces propagation losses. As such, the threshold power needed to activate SRS in a hollow core holey fiber would generally be reduced significantly, resulting in improved optical gain performance.

Figure 4:
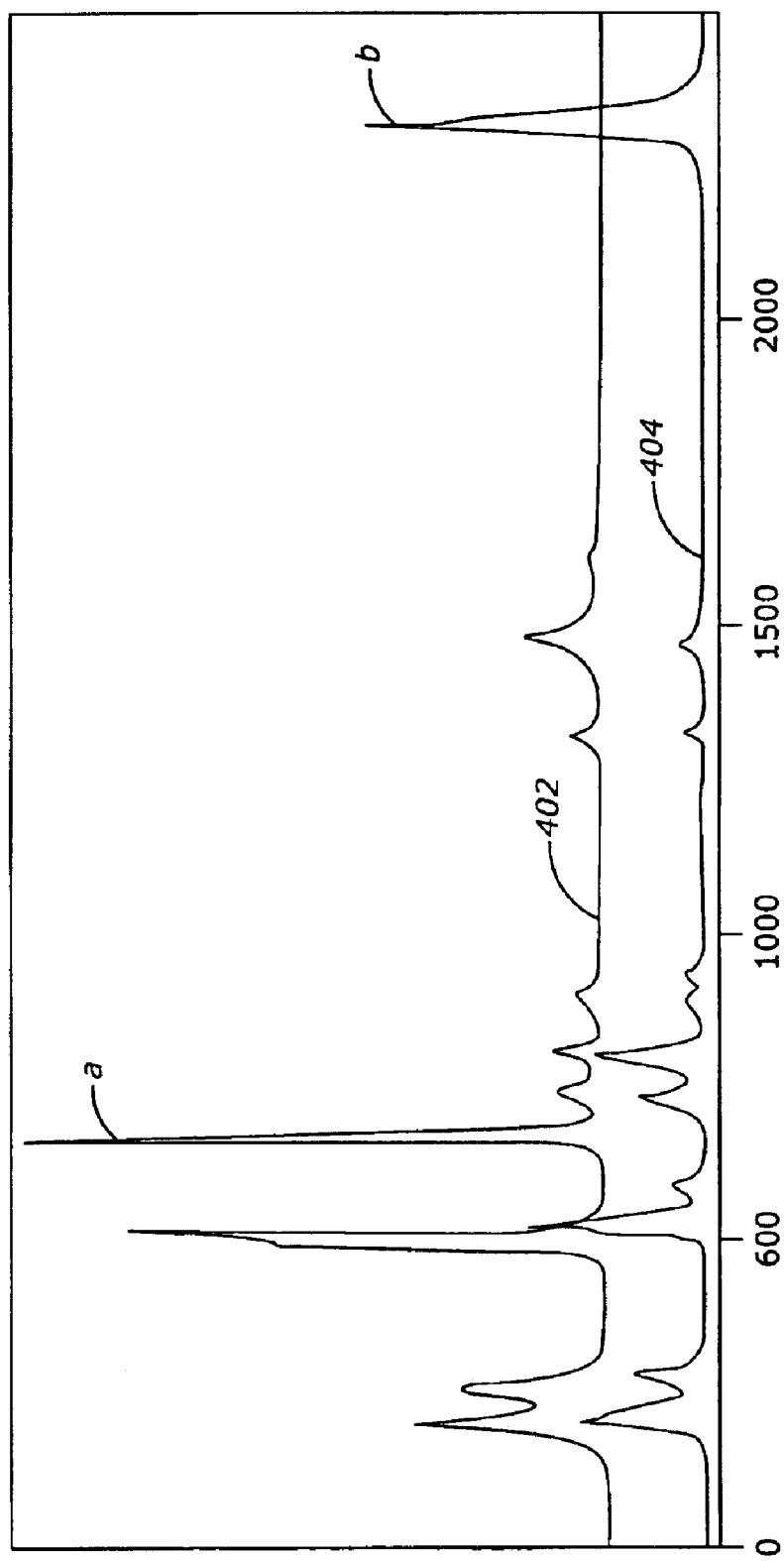
FIG. 4 is an illustration of Raman shift spectra for two substances.

Referring again to the exemplary embodiment shown in FIGS. 2 and 3, the filtered emissions beam 309 is routed to signal processor/detector 216 for spectroscopic analysis and substance identification. Typically, this analysis is based on the distinctive Raman spectral characteristics of beam 309, as previously described. An illustrative example of Raman spectra for two different substances (402, 404) plotted on the same set of axes is shown in FIG. 4. The y-axis represents Raman band intensity, and the x-axis represents the amount of Raman shift. Each spectrum has a characteristic set of peaks that allow it to be distinguished from the other. In this example, peak "a" is the distinguishing feature of spectrum 402, and peak "b" is the distinguishing feature of spectrum 404.

Figure 5:
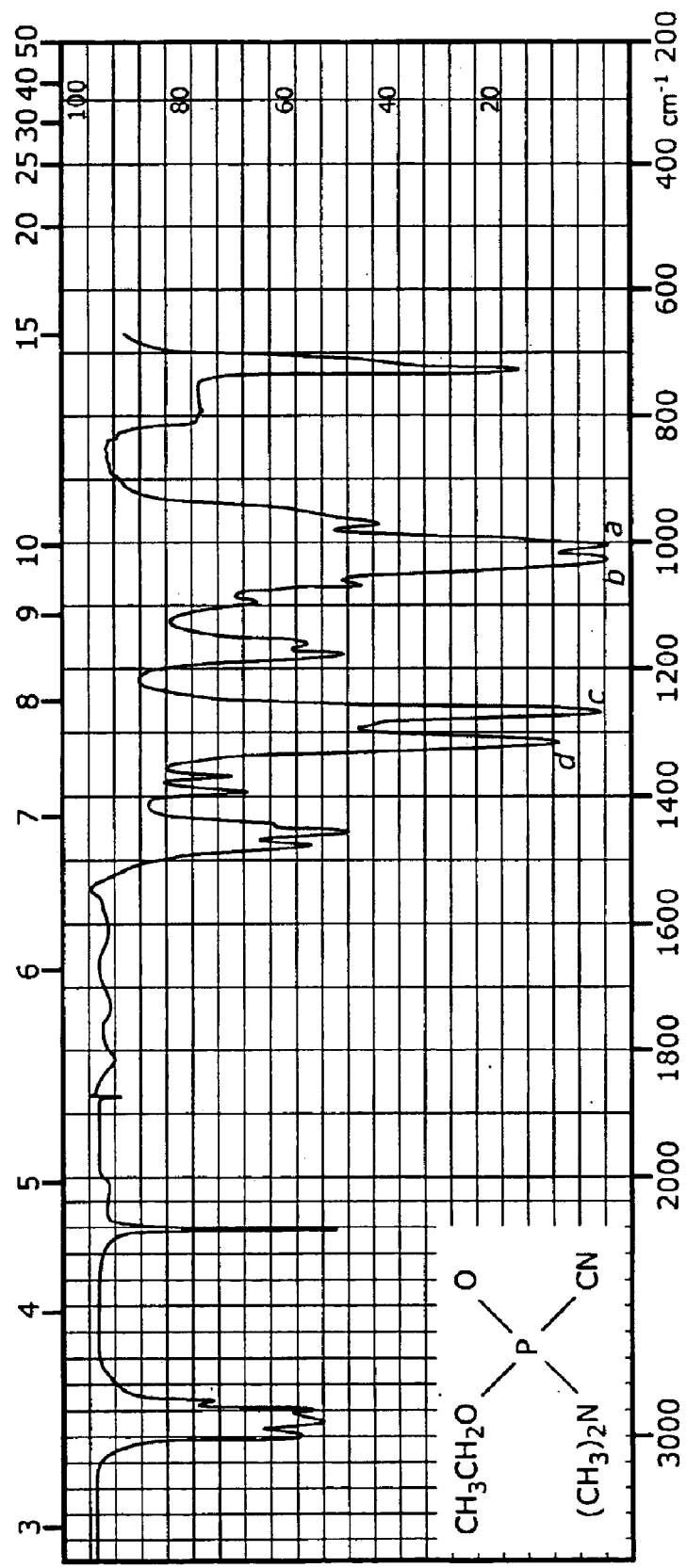
FIG. 5 is a Raman shift plot for Soman.
Figure 6:
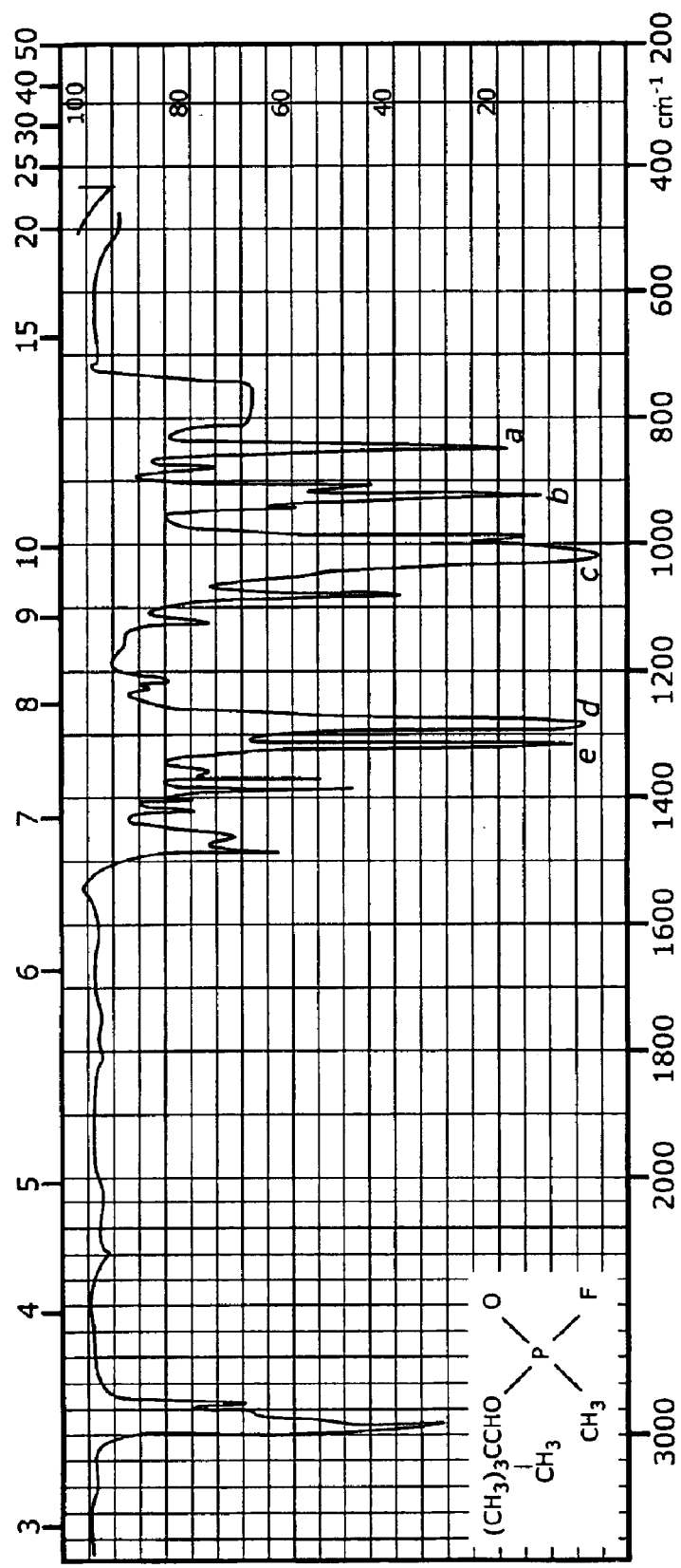
FIG. 6 is a Raman shift plot for Tabun.

Spectral plots for toxic nerve gases Soman and Tabun are shown in FIGS. 5 and 6, respectively, as typical examples of chemical warfare substances having specific Raman shift characteristics. In FIG. 5, for example, major peaks of the Soman spectrum appear at wave numbers of 1,000, 1,025, 1,270, and 1,318 $cm^{-1}$, as indicated by points a, b, c, and d, respectively. In FIG. 6, major peaks of the Tabun spectrum appear at wave numbers of 840, 920, 1,010, 1,281, and 1,318 $cm^{-1}$, as indicated by points a, b, c, d, and e, respectively.

Figure 7:
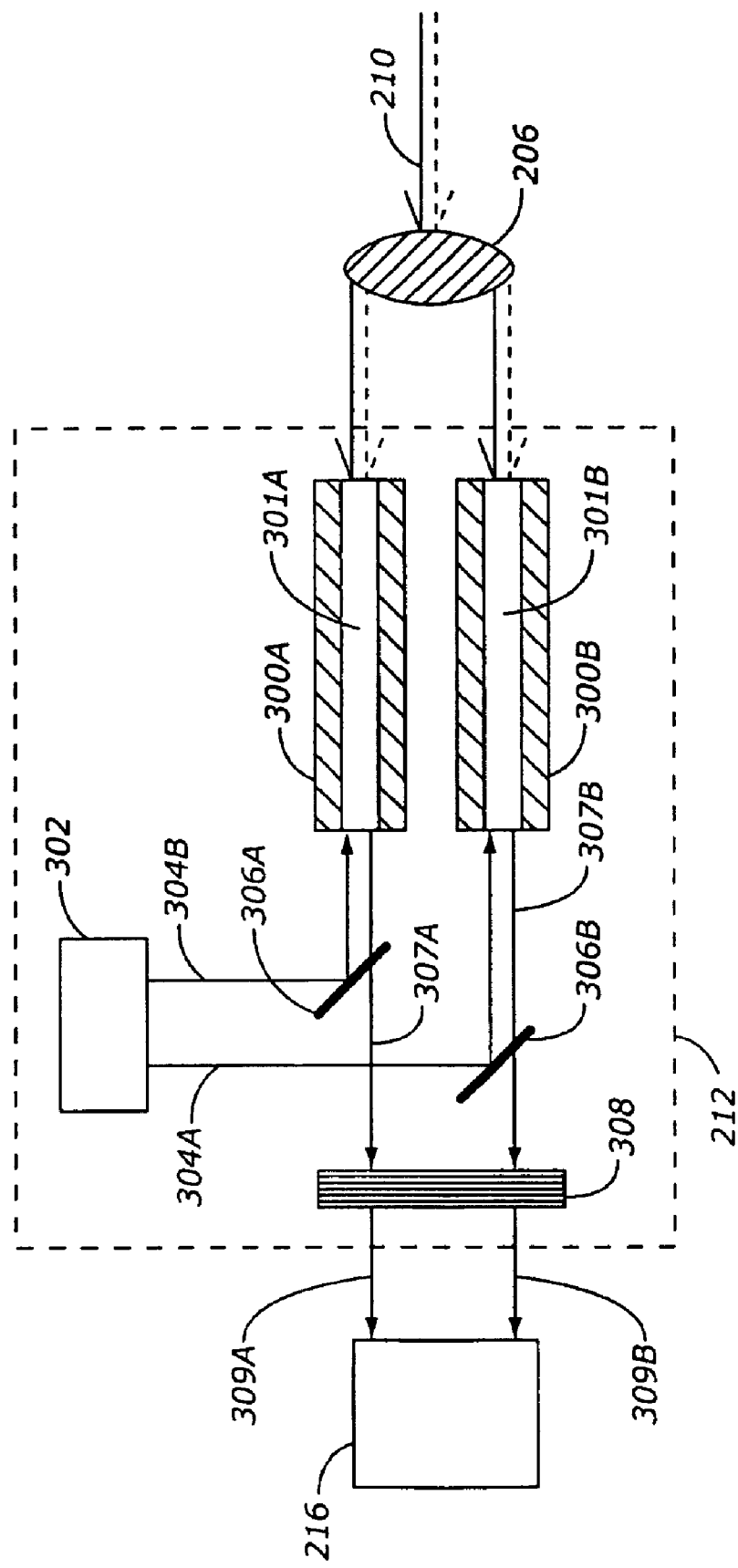
FIG. 7 is a block diagram of an exemplary embodiment of a multiple target sensing system.

The ability of the exemplary sensing system described herein to selectively amplify a particular molecular substance offers the potential for an alternative embodiment of a sensing system that can detect multiple target molecules simultaneously. To achieve multiple detection capability, a sensing system receiver can be configured with multiple hollow core fibers, with each fiber containing a different known substance sample. An exemplary embodiment of a multiple target sensing system configuration is illustrated in the simplified block diagram of FIG. 7, with like numerals from FIGS. 2 and 3 denoting like elements in FIG. 7.

As noted previously, an illuminating laser beam 204 is generally in the form of short pulses at high peak power levels. As such, an appropriately configured detection system 216 can make radar-like measurements of the reflected back-scatter signals to obtain range and direction data, in addition to the spectral information described above. Therefore, an exemplary embodiment of a CW detection system of the type described herein can not only identify a target molecule, but can also characterize its location.

Accordingly, the shortcomings of the prior art have been overcome by providing an improved remote sensing system for the detection of target substances, such as toxic chemicals and industrial pollutants. In the exemplary embodiment disclosed herein, the amplifying action of stimulated Raman scattering (SRS) within a hollow core holey fiber can result in a sensitive and selective detection system for a given molecular species. The sensitivity of the system can be enhanced because the Raman gain can be high with a low noise figure. In addition, the selectivity can be enhanced because the Raman gain lines are typically narrow, and can provide a spectral match that is virtually exact between the hollow core sample and the target substance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method of identifying a target substance, the method comprising the steps of:
   illuminating the target substance with a light to produce a back-scatter;
   providing the back-scatter to a sample of a known substance that has been pumped with a pump light, thereby stimulating Raman scattering in the known substance sample;
   detecting the characteristic spectrum of emission from the stimulated Raman scatter; and
   comparing the characteristic spectrum of the stimulated Raman scattering emissions from the sample to the characteristic spectrum of the known substance to thereby determine if the target substance matches the known substance.

2. The method of claim 1, wherein the target substance is a gas molecule.

3. The method of claim 1, wherein the illuminating light and the pump light have essentially identical output spectra.

4. The method of claim 1, wherein optical gain occurs at the frequencies of the stimulated Raman scattering emissions.

5. A sensing system for detecting the presence of a target substance within a target area, comprising:
   a transmitter configured to illuminate the target area to generate back-scatter light therefrom;
   a receiver containing a sample of a known substance and configured to selectively amplify the back-scatter light from the target area; and
   a detector configured to process the amplified back-scatter light, wherein the detector verifies the presence of the target substance when the amplified back-scatter light matches the sample of the known substance.

6. The sensing system of claim 5, wherein the transmitter comprises an illuminating laser and optics for directing an illuminating laser beam to the target area.

7. The sensing system of claim 6, wherein the receiver comprises a hollow core fiber containing a gaseous sample of the known substance, and the receiver further comprises optics configured to direct the back-scatter light from the target area into the hollow core fiber.

8. The sensing system of claim 7, wherein the receiver further comprises a laser pump having an output spectrum essentially identical to that of the illuminating laser, wherein the laser pump energizes the gaseous sample of the known substance within the hollow core fiber.

9. The sensing system of claim 8, wherein the receiver selectively amplifies a spectrum of the back-scatter light that matches the spectrum of the energized gaseous sample of the known substance.

10. The sensing system of claim 9, wherein the receiver selectively amplifies the matching spectrum of the back-scatter light by generating stimulated Raman scattering emissions in the hollow core fiber.

11. The sensing system of claim 10, wherein the hollow core fiber is a photonic-crystal fiber configured as a holey fiber.

12. The sensing system of claim 11, wherein the detector comprises signal processing circuitry configured to identify the spectrum of the amplified back-scatter light.

13. The sensing system of claim 12, wherein the detector further comprises signal processing circuitry configured to characterize the location of the amplified back-scatter light.

14. The sensing system of claim 11, wherein the receiver further comprises a plurality of hollow core fibers with each hollow core fiber containing a sample of a different known substance, wherein the sensing system simultaneously detects a plurality of known substances in the target substance.

15. A selective receiver for detecting reflected Raman scattered signals of a target substance, comprising:
   a hollow core fiber containing a pumped sample of a known substance having Raman scattered signals;
   an optical arrangement for introducing the reflected Raman scattered signals into the hollow core fiber, wherein the reflected Raman scattered signals are selectively amplified in the hollow core fiber by stimulated Raman scattering when the spectrum of the reflected Raman scattered signals matches the spectrum of the pumped sample of the known substance, and
   wherein the selective receiver verifies the presence of the target substance when the spectrum of the amplified Raman scattered signals matches the spectrum of the sample of the known substance.

16. The selective receiver of claim 15, wherein the hollow core fiber is a photonic-crystal fiber configured as a holey fiber.

* * * * *